(12) United States Patent
Gunji (10) Patent No.: US 8,216,143 B2
(45) Date of Patent: Jul. 10, 2012

(54) ULTRASONIC IMAGING APPARATUS, A METHOD FOR DISPLAYING A DIAGNOSTIC IMAGE, AND A MEDICAL APPARATUS

(75) Inventor: Takayuki Gunji, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1077 days.

(21) Appl. No.: 11/859,296

(22) Filed: Sep. 21, 2007

(65) Prior Publication Data

US 2008/0077012 A1  Mar. 27, 2008

(30) Foreign Application Priority Data

Sep. 22, 2006 (JP) ................. 2006-256786

(51) Int. Cl.
*A61B 8/00* (2006.01)
(52) U.S. Cl. ......... 600/440; 600/450; 600/427; 600/407
(58) Field of Classification Search .................. 600/437, 600/440, 443, 450, 407, 427; 382/128, 131
See application file for complete search history.

(56) References Cited

U.S. PATENT DOCUMENTS

| | | | | |
|---|---|---|---|---|
| 5,690,118 A * | 11/1997 | Sornmo et al. | ........... | 600/509 |
| 5,840,028 A * | 11/1998 | Chubachi et al. | ........... | 600/437 |
| 6,135,959 A | 10/2000 | Murashita et al. | | |
| 6,859,548 B2 * | 2/2005 | Yoshioka et al. | ........... | 382/128 |
| 7,031,504 B1 * | 4/2006 | Argiro et al. | ........... | 382/131 |
| 2004/0059205 A1 * | 3/2004 | Carlson et al. | ........... | 600/310 |
| 2006/0036172 A1 | 2/2006 | Abe | | |
| 2007/0036417 A1 * | 2/2007 | Argiro et al. | ........... | 382/131 |
| 2007/0129647 A1 * | 6/2007 | Lynn | ........... | 600/538 |
| 2008/0304730 A1 * | 12/2008 | Abe | ........... | 382/131 |

FOREIGN PATENT DOCUMENTS

| | | |
|---|---|---|
| JP | 7-250834 | 10/1995 |
| JP | 2004-49294 | 2/2004 |
| JP | 2006-26151 | 2/2006 |
| JP | 2006-314688 | 11/2006 |
| WO | WO 2005/008418 A2 | 1/2005 |
| WO | WO 2005/008418 A3 | 1/2005 |

* cited by examiner

*Primary Examiner* — Brian Casler
*Assistant Examiner* — Amanda Lauritzen
(74) *Attorney, Agent, or Firm* — Oblon, Spivak, McClelland, Maier & Neustadt, L.L.P.

(57) ABSTRACT

An ultrasonic transceiver obtains scanning data by transmitting ultrasound to a subject and receiving a reflected wave from the subject. A biological motion part measures, during said scanning, cyclic biological motion of said targeted organ and then calculates a measured waveform that shows motion in relation to time used for said biological motion. An image data generator converts the scanning data into image data shown in a specified coordinate system, and generates an ultrasonic tomographic image. A display controller superposes a standard waveform for a measured waveform, and a measured waveform for the latest cycle, so as to match a specified time phase for each waveform, and causes a display part to display these with the ultrasonic tomographic image.

20 Claims, 11 Drawing Sheets

| SETUP OF ABNORMAL MOTION DETECTION | | |
|---|---|---|
| 001 — SETUP OF ABNORMAL MOTION DETECTION | ● ON  ○ OFF | |
| 002 — STARTING REFERENCE POSITION FOR ELECTROCARDIOGRAPHIC WAVEFORM | ○ Q  ● R  ○ S  ○ T  ○ P | |
| 003 — TARGET FOR ABNORMAL MOTION DETECTION | ● ELECTROCARDIOGRAPHIC WAVEFORM  ○ BLOOD FLOW WAVEFORM  ○ WALL MOTION  ○ RANGE | |
| 004 — THRESHOLD | ELECTROCARDIOGRAPHIC WAVEFORM (mm) △ ±1.0 ▽ — 014 | BLOOD FLOW WAVEFORM (cc) △ ±8.0 ▽ — 024 | WALL MOTION (mm) △ ±2.5 ▽ — 034 | RANGE (cm2) △ ±0.5 ▽ — 044 |
| 005 — RANGE FOR AVERAGE CALCULATION | HEARTBEAT △ 4 ▽ | |
| 006 — UPON DETECTION OF ABNORMAL MOTION | ■ MESSAGE DISPLAY  □ AUTOMATIC Freeze  □ AUTOMATIC PLAY (ABNORMAL MOTION)  ■ AUTOMATIC PLAY (ABNORMAL MOTION + NORMAL MOTION) | |

STORE   END
007

ULTRASONIC IMAGING APPARATUS, A METHOD FOR DISPLAYING A DIAGNOSTIC IMAGE, AND A MEDICAL APPARATUS

BACKGROUND OF THE INVENTION

1. Field of the Invention

The present invention relates to an ultrasonic imaging apparatus for generating and displaying an ultrasonic tomographic image by ultrasonically scanning a cross-section of a subject, as well as detecting abnormal motion.

2. Description of the Related Art

An ultrasonic imaging apparatus is capable of obtaining an image in real-time showing, for example, a heartbeat simply by placing an ultrasonic probe on the surface of a subject. Therefore, the ultrasonic imaging apparatus has been used for diagnosing abnormal motion of the target organ, such as abnormality of the diastolic/systolic motion of a heart. The ultrasonic imaging apparatus is safer than other apparatus such as an X-ray diagnostic apparatus, an X-ray CT apparatus, or an MRI apparatus, so it can repeat examinations. Further, the ultrasonic imaging apparatus has a small system scale, so it is simple in that, for example, examinations can be easily performed, even if it is moved to a bedside. Furthermore, the ultrasound diagnosis does not cause effects from exposure, unlike X-rays, so it can be used in an Obstetrics Department or a home healthcare.

Figure 1:
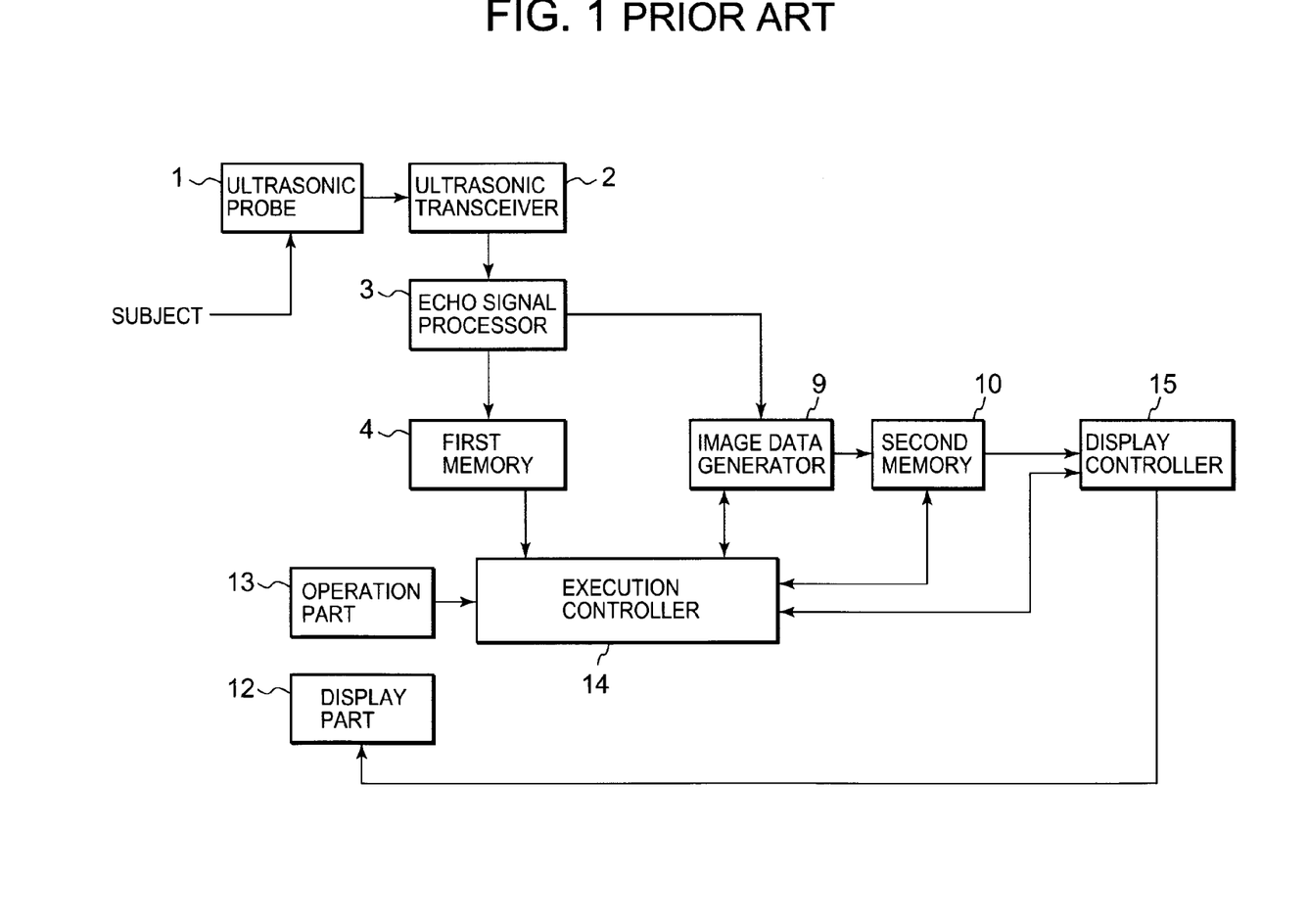
FIG. 1 is a block diagram of a conventional ultrasonic image diagnostic apparatus.

The configuration of a conventional ultrasonic imaging apparatus that generates ultrasonic tomographic images is shown in FIG. 1. FIG. 1 is a block diagram of a conventional ultrasonic imaging apparatus. For an ultrasonic probe 1 shown in FIG. 1, a so-called one-dimensional ultrasonic probe in which ultrasonic transducers are arranged in a specified direction (scanning direction) or a two-dimensional ultrasonic probe in which ultrasonic transducers are arranged in a matrix are used.

An ultrasonic transceiver 2 activates the ultrasonic probe 1 according to a control signal that has been output from an execution controller 14. Subsequently, the ultrasonic transceiver 2 transmits/receives ultrasound, and scans the specified area.

An echo signal processor 3 comprises a digital receiver mainly for performing processes such as filtering and digital gain adjustment by receiving data that has been output from the transceiver 3. Oscillation information for an echo performed with these processes is called raw data. The echo signal processor 3 stores this raw data in a first memory 4.

An image data generator 9 comprises a B mode processing circuit or a CFM processing circuit. Data that has been output from the digital receiver is processed with the specified process in any processing circuit. The B mode processing circuit generates images based on the oscillation information and generates B mode ultrasonic raster data from an echo signal. The CFM processing circuit generates images for circulating the blood flow and generates a color ultrasonic raster data. Furthermore, the image data generator 9 has a digital scan converter. The digital scan converter converts the ultrasonic raster data into image data shown at orthogonal coordinates in order to obtain an image shown at the orthogonal coordinates. The image data generator 9 stores ultrasonic imaging data shown at orthogonal coordinates in a second memory 10.

A display controller 15 instructs a display part 12 to display the ultrasonic tomographic image that is the ultrasonic image data stored in the second memory 10. Referring to the ultrasonic tomographic image displayed on the display part 12 thereby makes it possible for a doctor to make a diagnosis.

Conventionally, a method has been proposed for detecting abnormal motion from the target organ using an ultrasonic diagnostic apparatus. The method is, for example, a stress echo function, i.e., the art of diagnosing by comparison with normal motion by subjecting the heart patient to exercise stress and pharmacological stress (Japanese Unexamined Patent Application Publication No. 2006-26151).

Additionally, a measured waveform (a biological waveform such as an electrocardiographic waveform) shows a waveform according to time. However, the measured waveform is sequentially scrolled. Therefore, it has been difficult for an operator to find changes that appear in the measured waveform. Accordingly, it has also been difficult for an operator to find abnormalities based on changes in the measured waveform.

Furthermore, in diagnosis performed by stress echo, abnormal motion is ascertained by reference to an image, so it relies on the experience of an operator, which has made measurement complicated and also makes the shortening of measurement time difficult.

SUMMARY OF THE INVENTION

The present invention is intended to provide an ultrasonic diagnostic apparatus for displaying an ultrasonic tomographic image of a subject, as well as displaying by superposing a measured waveform on a standard waveform. As used herein, a standard waveform means a waveform that is used as a standard in order to compare waveform changes in measured waveforms. Additionally, the present invention is also intended to provide an ultrasonic diagnostic apparatus for automatically detecting abnormal motion of the target organ of a subject.

An aspect of the present invention is an ultrasonic diagnostic apparatus that scans a cross-section of the target organ of a subject, generates an ultrasonic tomographic image based on an obtained echo signal, and displays said ultrasonic tomographic image on a display part. The ultrasonic diagnostic apparatus comprises: a biological motion-measuring part configured to measure cyclic biological motion of said targeted organ during said scanning so as to calculate a measured waveform that shows motion in relation to time used for said biological motion; and a display controller configured to cause a display part to display a standard waveform for said measured waveform, and a measured waveform for the latest cycle by means of superposition, so as to match a specified time phase for each waveform. The relevant art can be applied to an ultrasonic imaging apparatus, a method for displaying a diagnostic image, and a medical apparatus.

According to the relevant art, the ultrasonic tomographic image generated by ultrasonically scanning the subject is displayed, and furthermore the measured waveform and the standard waveform are additionally superposed and displayed. This makes it possible to objectively recognize the changes in measured waveforms in the target organ of the subject and thus contribute to an accurate diagnosis.

DETAILED DESCRIPTION OF THE EMBODIMENTS

Embodiment 1

Figure 2:
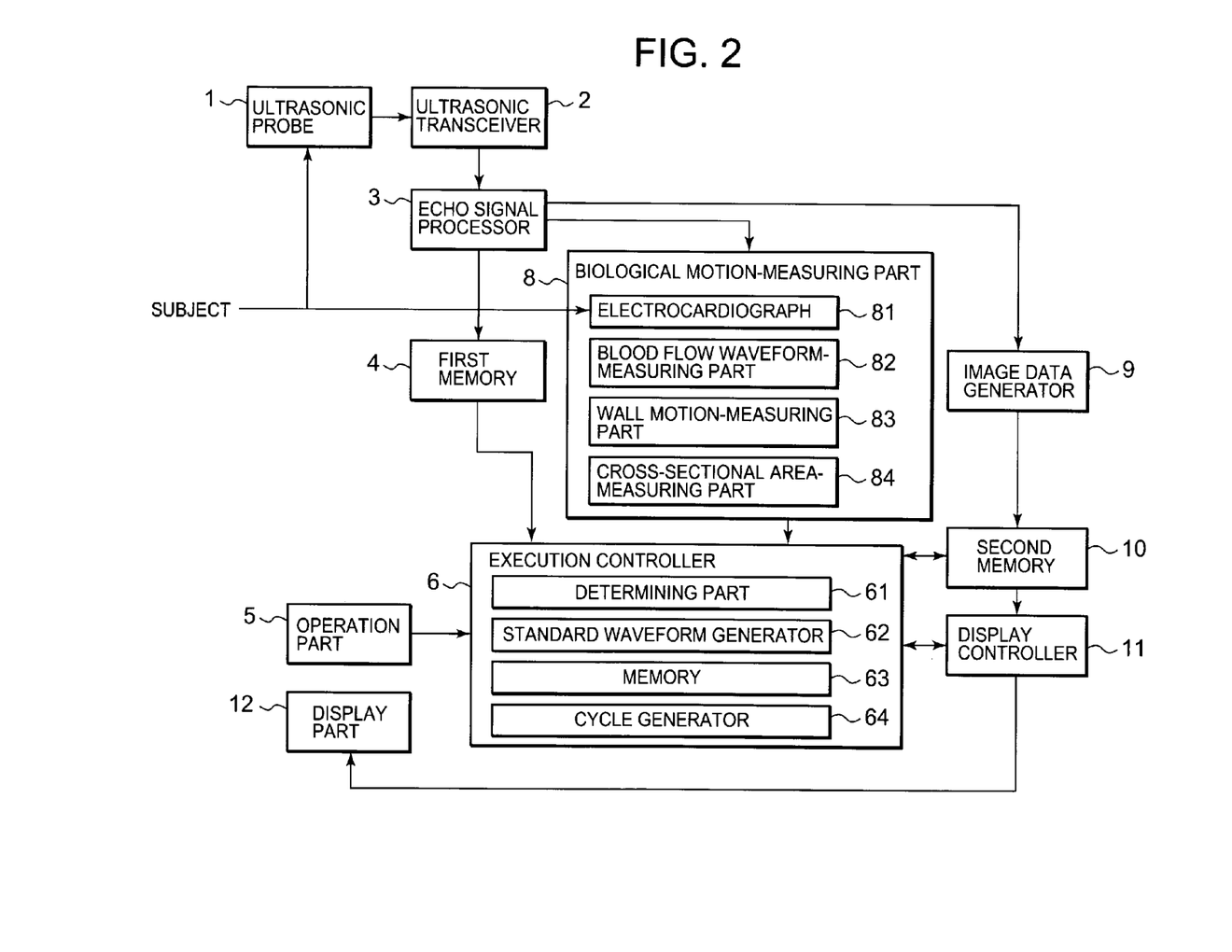
FIG. 2 is a block diagram of an ultrasonic image diagnostic apparatus according to the present invention.

An ultrasonic diagnostic apparatus according to Embodiment 1 of the present invention will be described below with reference to FIG. 2 to FIG. 8. In FIG. 2, components having the same code as FIG. 1 described in the background have the same function, so the explanation for components having the same code will be omitted. The case in which a biological waveform is used as a measured waveform will be described below. In particular, the case in which an electrocardiographic waveform is used out of the biological waveform will mainly be described.

Figure 4:
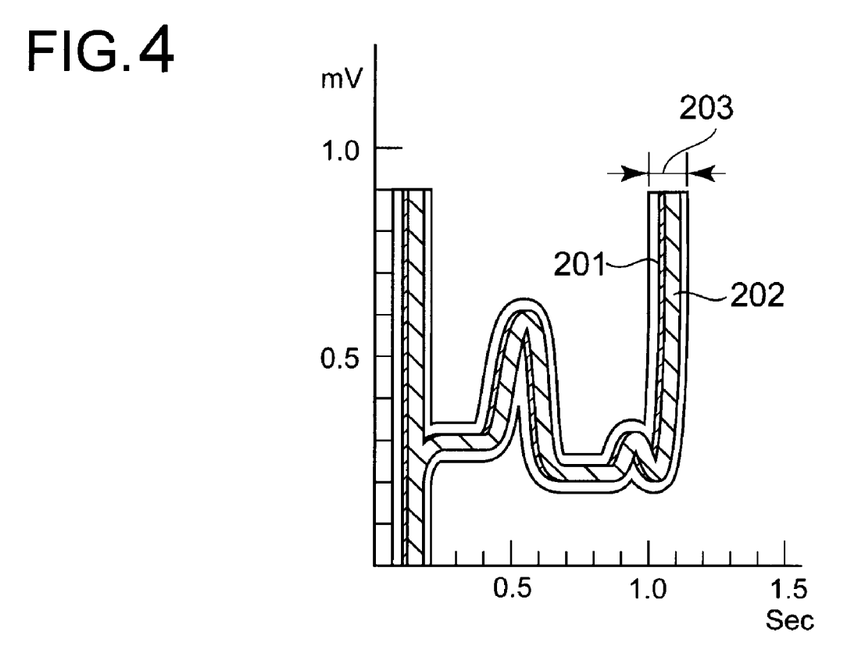
FIG. 4 is a real-time graph at the time of normal motion.

FIG. 2 shows a biological motion-measuring part 8 comprising an electrocardiograph 81, a blood flow waveform-measuring part 82 for performing Doppler processing, wall motion-measuring part 83, and a cross-sectional area-measuring part 84. The electrocardiograph 81 generates an electrocardiogram of a subject and obtains an electrocardiographic waveform (FIG. 4 shows a part thereof). The blood flow waveform-measuring part 82 generates data having blood flow information by receiving an echo signal from the echo signal processor 3, extracting a Doppler-shift frequency component, and further performing, for example, FFT (Fast Fourier transform) process, etc. Examples of the blood flow information include velocity, dispersion, power, and the like, and the blood flow information is obtained as binary information. Subsequently, the blood flow waveform is obtained. The wall motion-measuring part 83 operates so as to extract one point in a heart wall based on the echo signal transmitted from the echo signal processor 3, measure the distance between that point and a predetermined center point in the heart, measure the change in that distance, and thus obtain the displacement of wall motion that is to be a time change of said distance. Additionally, the cross-sectional area-measuring part 84 operates so as to trace the circumference of four areas, including the left ventricle, the right ventricle, the left atrium, and the right atrium of a heart, which is the target organ of the subject, based on the echo signal transmitted from the echo signal processor 3, measure each area, and obtain the amount of change in the cross-sectional area that is to be a time change of said cross-sectional area. At this stage, in the present embodiment, four types of biological waveforms, including the electrocardiographic waveform, the blood flow waveform, the displacement of the wall motion, and the amount of change in the cross-sectional area, are targeted for detecting abnormal motion, but this is not specially limited if it is a cyclical biological motion, and thus, other information regarding cyclical biological motion may be targeted for detecting abnormal motion.

An execution controller 6 manages and controls all operation. The execution controller 6 controls an ultrasonic transceiver 2 and causes it to scan the desired range of the biological body. Additionally, the execution controller 6 receives the type of biological motion targeted for detecting abnormal motion from an operation part 5, and detects abnormalities in said biological motion. The execution controller 6 shown in FIG. 2 comprises a determining part 61, a standard waveform generator 62, a memory 63, and a cycle generator 64. By way of example, the present embodiment mainly considers the case in which the electrocardiographic waveform is selected for detecting abnormal motion. The case in which the execution controller 6 mainly detects abnormal motion in the electrocardiographic waveform will be described below.

The execution controller 6 stores, in a memory 63, the electrocardiographic waveform, the blood flow waveform, the displacement of the wall motion, and the amount of change in the cross-sectional area, which have been transmitted from the biological motion-measuring part 8.

The cycle generator 64 operates so as to calculate the amount of change of a feature point in the electrocardiographic waveform based on the biological waveform received from the biological motion-measuring part 8. The cycle generator 64 determine the position in the electrocardiographic waveform for the starting reference position (i.e., one of Q-wave, R-wave, S-wave, or T-wave) that has been input according to that amount of change, according to the starting reference position of the electrocardiographic waveform received by the operation part 5. The cycle generator 64 then divides the electrocardiographic waveform into individual cycles, based on the starting reference position. As used herein, a starting reference position for the electrocardiographic waveform means any one of Q wave, R-wave, S-wave, or T-wave in the electrocardiographic waveform. In this respect, the blood flow waveform, the displacement of the wall motion, and the amount of change in the cross-sectional area also moves cyclically based on the heartbeat. Therefore, even in the case of the blood flow waveform, the displacement of the wall motion, and the amount of change in the cross-sectional area, one cycle for a targeted biological waveform can be obtained by using a starting reference position of the electrocardiographic waveform in the same way as the electrocardiographic waveform. In the present embodiment, by way of example, the R-wave position in the electrocardiographic waveform is used as a starting reference position (refer to FIG. 4). Accordingly, the execution controller 6 divides the electrocardiographic waveform from the R-wave to the next R-wave as one cycle, and a continuous electrocardiographic waveform is composed of a plurality of one-cycle electrocardiographic waveform.

Receiving a range for calculating the average from the operation part 5, the standard waveform generator 62 takes an average for cycles between a previous cycle for the latest cycle and a cycle before the range for calculating the average, in order to calculate the standard waveform of the biological motion that is to be targeted for detecting abnormal motion. As used herein, a "standard waveform" means an average biological waveform for the subject as a standard for confirming the amount of change for the biological waveform. By way of example, the present embodiment considers the case in which 4 is input as a range for calculating the average. Hereinafter, the electrocardiographic waveform that is targeted for determining whether it is abnormal motion is referred to as "the latest electrocardiographic waveform".

The standard waveform generator 62 retrieves, from the memory 63, the last four electrocardiographic waveforms counted from the previous cycle of the latest electrocardiographic waveform. Then, the standard waveform generator 62 calculates a weighted average for those four electrocardiographic waveforms, and uses it as a standard waveform. At this stage, so as to detect the abnormality when the difference between the latest electrocardiographic waveform and the most preceding electrocardiographic waveform is large, the present embodiment calculates the average by using most preceding electrocardiographic waveform as a standard waveform. Meanwhile, the standard waveform may be calculated, for example, by preliminarily obtaining the electrocardiographic waveform obtained in the normal condition and then taking an average from them. This electrocardiographic waveform obtained in the normal condition also may be obtained from the past data of the subject, and then the average may be preliminarily calculated. Additionally, the standard waveform can be separated according to the application for the diagnosis. For example, the standard value for pre-dosage and post-dosage of the drug as well as the standard value for pre-exercise stress and post-exercise stress, can be managed.

Furthermore, the standard waveform generator 62 operates the same, even if the blood flow waveform, the displacement of the wall motion, or the amount of change in the cross-sectional area is targeted for detecting abnormal motion. For example, when 4 is input as an range for calculating the average, the standard waveform generator 62 can operate to retrieve, from the memory 63, the last four electrocardiographic waveforms counted from the previous cycle waveform for each latest electrocardiographic waveform (that is targeted for the determination of abnormal motion). Then, the standard waveform generator 62 calculates a weighted average for those four electrocardiographic waveforms, and calculates the standard waveform corresponding to each waveform.

The determination part 61 operates so as to compare the standard waveform with the latest electrocardiographic waveform, determine whether the latest electrocardiographic waveform is abnormal, based on the threshold received from the operation part 5, according to whether the difference between the standard waveform and the latest electrocardiographic waveform exceeds that threshold, and detect that the heart that is an organ targeted for detecting abnormal motion causes abnormal motion. The top-to-bottom range by the standard waveform with the threshold added is aimed at "a range set as normal motion" in the present invention. In other words, when this threshold is exceeded, it is considered that the targeted section performs a motion that cannot be deemed as normal motion. As used herein, an electrocardiogram is represented as a graph when a longitudinal axis is an electrocardiographic electrical potential and a lateral axis is a time. Provided that the threshold is set based on the electrical potential, a unit of the threshold for the electrocardiographic waveform is set as a height for the electrocardiographic waveform when the electrical potential for the electrocardiographic waveform 0.1 mV is set as a 1 mm in the electrocardiogram. In the present embodiment, by way of example, it is provided that the threshold of the electrocardiographic waveform is set as 0.05 sec. The determining part 61 compares each point in one cycle for the standard waveform and the latest electrocardiographic waveform, and determines abnormal motion if the difference is 0.05 sec or more. As used herein, one cycle of the electrocardiographic waveform is approximately 1 sec, and therefore the fact there is a difference of 0.05 sec from the average value, means that a difference of approximately 5% is caused, and the time difference of 5% is considered as a substantial difference for a heart motion. Therefore, the present embodiment determines the abnormal if the difference of 0.05 sec or more is caused. Additionally, if the threshold is set based on the electrical potential, the threshold for the electrocardiographic waveform is set as 1 mm. The determining part 61 determines abnormal motion if the difference of 1 mm or more, by comparing each point in one cycle for the standard waveform and the latest electrocardiographic waveform. As used herein, the R-wave for the electrocardiogram is approximately 1.0 mV as the highest electrical potential, and therefore the fact there is a difference of 1 mm (0.1 mV) from the average value, means that a difference of approximately 10% is caused, the case of which is to be determined as abnormal. Meanwhile, the threshold may be smaller in order to detect abnormal motion at the earlier stage, or the threshold may be larger in order to detect abnormal motion only for the large abnormal case. Additionally, in the present embodiment, the absolute value of the difference amount is used as a threshold, but this may be a relative amount and represented as a ratio (%) based on the standard waveform.

Furthermore, even if the blood flow waveform, the displacement of the wall motion, or the amount of change in the cross-sectional area is targeted for detecting abnormal motion, the determining part 61 can operate similarly as follows: receiving, from the operation part 5, as a threshold, the information about how much difference (cc) is caused from the standard waveform in the case of the blood flow waveform, how much difference (mm) is caused from the standard waveform in the case of the displacement of the wall motion, or how much difference ($cm^2$) is caused from the standard waveform in the case of the amount of change in the cross-sectional area; comparing the waveform to be determined abnormality with the standard waveform calculated by the standard waveform generator 62; determining whether the blood flow waveform, the displacement of the wall motion, or the amount of change in the cross-sectional area is abnormal, according to whether that difference exceeds said threshold; and therefore detecting that the organ targeted for detecting abnormal motion causes abnormal motion.

Figure 10A:
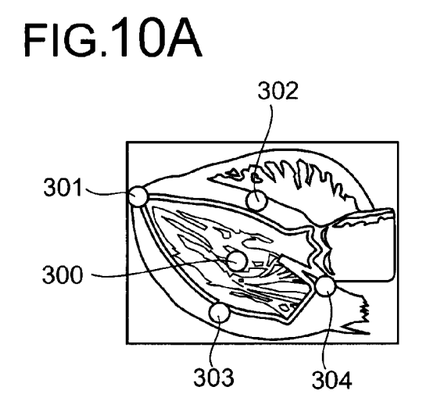
FIG. 10A is an illustration of a heart in diastolic state.
Figure 10B:
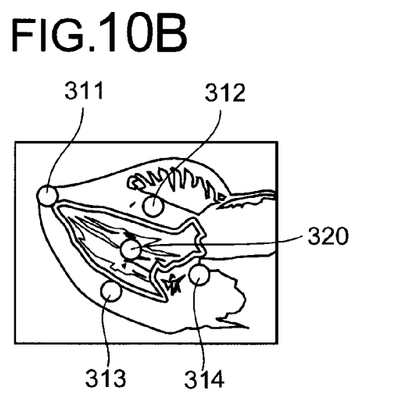
FIG. 10B is an illustration of a heart in systolic state.

For example, the displacement of the wall motion is targeted for the observation, as will be described with reference to FIG. 10. FIG. 10 illustrates a method for measuring the displacement of the wall motion. FIG. 10A illustrates a heart during diastole. FIG. 10B illustrates a heart during systole. As shown in FIG. 10, the wall motion-measuring part 83 extracts 4 points targeted for measuring the displacement of the heart wall, for example, a point 301, a point 302, a point 303, and a point 304 shown in FIG. 10A, based on the echo signal transmitted from the echo signal processor 3. Then, the wall motion-measuring part 83 measures the distance from a predetermined center point, for example, a center point 300 shown in FIG. 10, to each point. In the same way, the displacement of the heart wall is measured every 0.1 second. For example, in the FIG. 10B, the distance from the center point 310 to the point 311, the point 312, the point 313, and the point 314 are measured. By repeating the abovementioned operation, the wall-motion measuring part 83 calculates the displacement of the wall motion that is to be a time change of the displacement during one heat in each point.

Then, the standard waveform generator 62 receives the displacement of the wall motion that has been divided into every one heartbeat by the cycle generator 64. The standard waveform generator 62, then, calculates the standard waveform of the displacement of the wall motion by taking an average for cycles of the last 4 heartbeats counted from the previous cycle of the latest cycle.

The determining part 61 receives, from the standard waveform generator 62, an input of the standard waveform of the displacement of the wall motion. The determining part 61 determines whether it is abnormal according to whether the difference between the input standard waveform and the latest displacement of the wall motion exceeds the threshold received from the operation part 5. At this stage, the wall motion during one heartbeat begins from diastole (shown in FIG. 10A) and returns to diastole (shown in FIG. 10A) through systole (shown in FIG. 10B). In the case of wall motion, unlike the electrocardiogram for measuring the voltage, the difference in the displacement is greatest during systole if diastole is set as a standard. Accordingly, the range set as normal motion needs to be provided with some allowance at the time of systole. Therefore, in the case of such wall motion, the threshold during one heartbeat may not be the same, and may not be fixed so that a larger threshold is set during the period up to systole, and a smaller threshold is set during the period from systole to diastole. By doing so, the range set as normal motion can be improved appropriately. In that case, the determining part 61 determines whether it is abnormal based on the threshold that changes every elapsed time during one heartbeat.

The execution controller 6 receives the determination for detecting abnormal motion generated in the determining part 61, and then obtains, from the second memory, the ultrasonic tomographic image corresponding to the latest electrocardiographic waveform. Additionally, the execution controller 6 receives the standard waveform of the electrocardiographic waveform from the standard waveform generator 62. Subsequently, the execution controller 6 transmits, to the display controller 11, the information about abnormal motion detection, the latest electrocardiographic waveform, the ultrasonic tomographic image corresponding to the latest electrocardiographic waveform, the standard waveform of the electrocardiographic waveform, and the threshold.

Additionally, even if the blood flow waveform, the displacement of the wall motion, or the amount of change in the cross-sectional area is targeted for detecting abnormal motion, the execution controller 6 operates the same to receive the determination for detecting abnormal motion generated in the determining part 61, and then obtains, from the second memory, the ultrasonic tomographic image corresponding to the waveform that is targeted for detecting abnormal motion in the blood waveform, the displacement of the wall motion, or the amount of change of the cross-sectional area. Furthermore, the execution controller 6 receives, from the standard waveform generator 62, the standard waveform of the blood waveform, the displacement of the wall motion, or the amount of change of the cross-sectional area that is targeted for detecting abnormal motion. Additionally, the execution controller 6 transmits, to the display controller 11, the information about abnormal motion detection, the standard waveform, the threshold, and the ultrasonic tomographic image corresponding to the waveform that is targeted for detecting abnormal motion of the blood waveform, the displacement of the wall motion, or the amount of change of the cross-sectional area.

Figure 3:
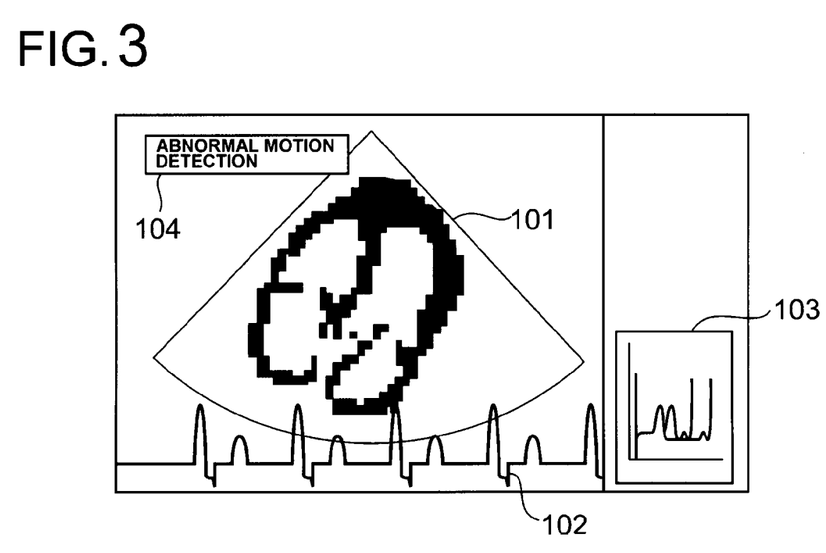
FIG. 3 is an explanatory diagram of a display screen at the time of abnormal motion detection.

Once the information is received from the execution controller 6, the display controller 11 displays a normal ultrasonic tomographic image 101 and a normal electrocardiographic waveform 102, as shown in FIG. 3. As used herein, a normal ultrasonic tomographic image 101 and a normal electrocardiographic waveform 102 are respectively an ultrasonic tomographic image and an electrocardiographic waveform, which are displayed in real-time when scanning is performed by ultrasound. Additionally, the display controller 11 displays a real-time graph 103 showing the electrocardiographic waveform so that it is not superposed on the ultrasonic tomographic image 101 and the electrocardiographic waveform 102.

The real-time graph 103 will be herein described with reference to FIG. 4 and FIG. 5.

As shown in FIG. 4, the real-time graph 103 is displayed by superposing the latest electrocardiographic waveform 202, the standard waveform 201 for the latest electrocardiographic waveform, the threshold range 203, based on the starting reference position calculated by the cycle generator 64 (in the case of the present embodiment, a time for the top of the R-wave). The threshold range 203 means the range set as normal motion as described above. In this figure, the longitudinal axis is represented as an electrical potential (mV), and the lateral axis is represented as a time (sec). Additionally, in the longitudinal axis, 0.1 mV is set as 1 mm. The lateral axis is divided into the time for individual cycles. Subsequently, the display controller 11 real-timely displays by updating the standard waveform 201, the latest electrocardiographic waveform 202, and the threshold range 203, whenever the latest electrocardiographic waveform 202 is updated, with the biological motion in the normal condition. As used herein, the threshold range 203 means the area which is displayed by setting, in each point of the standard waveform 201, a part added with the input threshold as an upper limit and a part deducted with the input threshold as a lower limit, and putting gray color in the area between those limits. In other words, when it falls out of the threshold range 203, it means that it exceeds the threshold, so a doctor can determine whether it is abnormal, according to whether the electrocardiographic waveform falls within the threshold range 203. In the present embodiment, the range that is added with ±0.05 sec to the time on the lateral axis in each point of the standard waveform 201, is represented as the threshold range 203. If the latest electrocardiographic waveform 202 is in the normal condition, the latest electrocardiographic waveform 202 will fall within the threshold range 203, as shown in FIG. 4.

Furthermore, in the present embodiment, a time difference is used as a value for a threshold set, but an electrical potential difference can be used as this threshold set. For example, if the electrical potential difference is used as a threshold set, the range that is added with ±1 mm to the electrical potential on the longitudinal axis in each point of the standard waveform 201 shown in FIG. 4 will be represented as a threshold range.

Additionally, even if the blood flow waveform, the displacement of the wall motion, and the amount of change in the cross-sectional area are targeted for detecting abnormal motion, this real-time graph 103 is also displayed by superposing the waveform targeted for determining abnormal motion in the blood flow waveform, the displacement of the wall motion, and the amount of change in the cross-sectional area, the standard waveform corresponding to said waveform, and the threshold range, based on the starting reference position of the electrocardiographic waveform.

Figure 11:
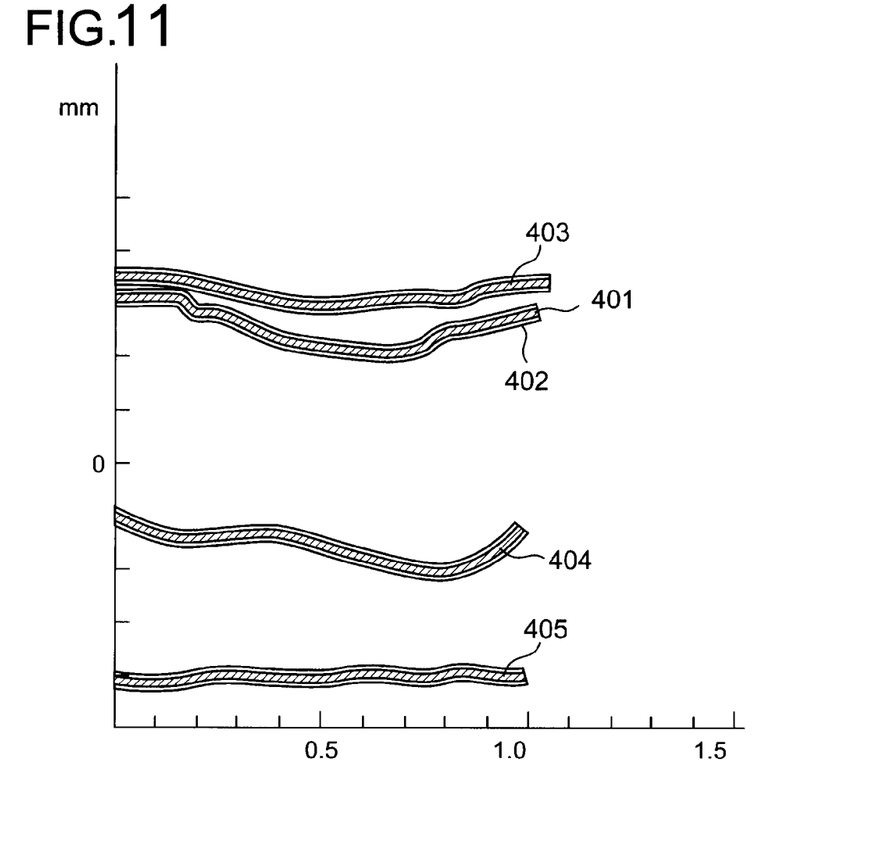
FIG. 11 is a graph showing superposition of a standard waveform and a range set as normal motion for the case of the displacement of wall motion observed at each point of a heart.

For example, a display for the standard waveform as well as the range set as normal motion when the displacement of the wall motion is targeted for the observation, will be described with reference to FIG. 11. FIG. 11 is a graph showing by superposing the standard waveform and the range set as normal motion for the case of the displacement for wall motion at each point of a heart. The standard waveform 401, 403, 404, and 405 shown in FIG. 11 respectively represent the standard waveform for the point 301, 302, 304, 303 shown in FIG. 10A. The threshold range 402 represents the threshold range for the standard waveform 401. Received the information from the execution controller 6, the display controller 11 displays the ultrasonic tomographic image 101 and the electrocardiographic waveform 102. Additionally, the display controller 11 displays the real-time graph 103 showing the displacement of the wall motion so that it is not superposed on the ultrasonic tomographic image 101 and the electrocardiographic waveform 102. A graph that the standard waveform 401 and the threshold range 402 are superposed and displayed in this real-time graph 103 showing the displacement of the wall motion, is shown in FIG. 11. The actual real-time graph 103 makes it possible to realize, at a glance, the change of the displacement of the wall motion by superposing and displaying the latest displacement of the wall motion on the graph shown in FIG. 11. Additionally, the graph shown in FIG. 11 shows the case in which the threshold width is set as fixed as shown in the threshold range 402. Meanwhile, to improve appropriately the range set as normal motion, the threshold range 402 shown in FIG. 11 is displayed so that the width is broader at the center part and narrower at the adjacent of both ends, in the case as described above that the smaller threshold is set during the diastole, and the larger threshold is set during the systole.

If the determining part 61 determines the abnormality, the display controller 11 will receive the information from the execution controller 6 and displays an alert 104 about abnormal motion detection over the display of the normal ultrasonic tomographic image 101 and the normal electrocardiographic waveform 102, as shown in FIG. 3. Additionally, the display controller 11 holds up the condition that the standard waveform of the electrocardiographic waveform, the threshold range, and the latest electrocardiographic waveform obtained at the time of detecting abnormal motion, are superposed on the real-time graph 103 located on the right side. In other words, the display controller 11 continuously instructs the display part 12 to display the condition that the standard waveform of the electrocardiographic waveform, the threshold range, and the latest electrocardiographic waveform obtained at the time of detecting abnormal motion are superposed on the real-time graph 103 located on the right side. Additionally, as other display methods, the ultrasonic tomographic image obtained in the abnormal condition may be continuously displayed together with the real-time graph obtained in the abnormal condition. As described above, this display controller 11 repeatedly instructs the display part 12 to display, the ultrasonic tomographic image 105 and the electrocardiographic waveform obtained in the abnormal condition 106. In other words, "the condition that the standard waveform of the electrocardiographic waveform, the threshold range, and the latest electrocardiographic waveform obtained at the time of abnormal motion detection, are displayed on the display part, is held up" in the present invention.

Additionally, even if the blood flow waveform, the displacement of the wall motion, or the amount of change in the cross-sectional area, is targeted for detecting abnormal motion, the same operation will be performed. In other words, when the determining part 61 determines that it is abnormal, the display part 11 displays the alert 104 about abnormal motion detection over the display of the normal ultrasonic tomographic image 101 and each normal waveform, and holds up the condition that the standard waveform of the targeted waveform, the threshold range corresponding to that, and the waveform for the blood flow waveform, the displacement of the wall motion, or the amount of change for the cross-sectional amount, which are obtained at the time of abnormal motion detection, are superposed and displayed on the real-time graph 103 to the right of the display.

Figure 5:
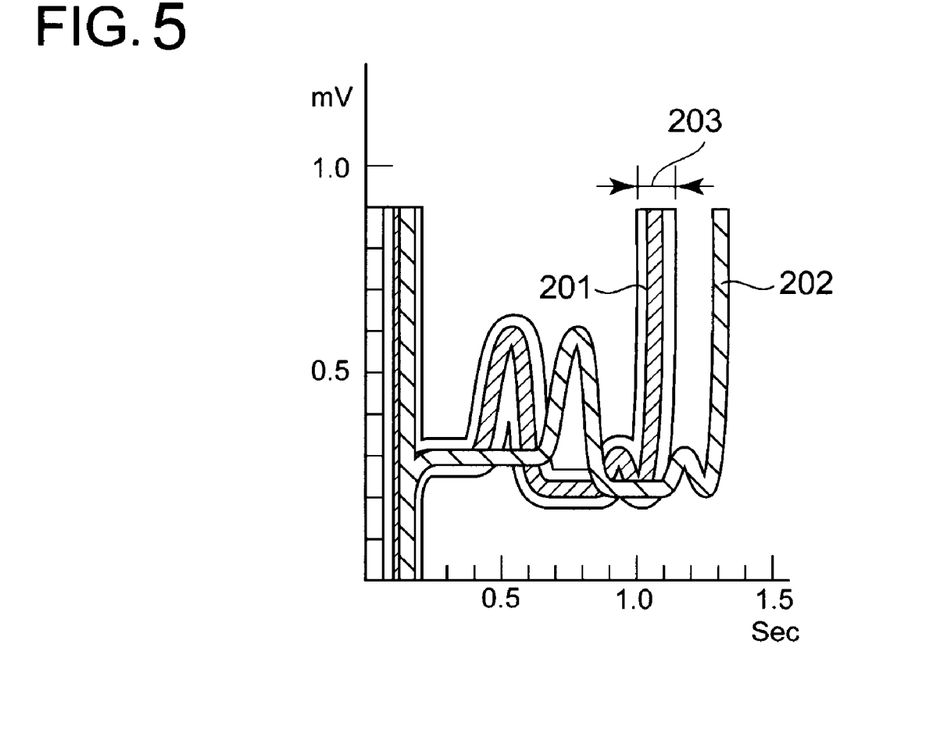
FIG. 5 is a real-time graph during abnormal motion detection.

Subsequently, when abnormal motion for the targeted organ is detected in the latest electrocardiographic waveform 202, the latest electrocardiographic waveform 202 falls out of the threshold range 203, as shown in FIG. 5. At this stage, the unit used for the longitudinal axis and the lateral axis in FIG. 5 is the same as the one for the graph in FIG. 4. In this way, the relation between the threshold range 203 and the latest electrocardiographic waveform 202 is visually shown, and therefore a doctor can understand the change for the waveform at a glance, and realize that abnormal motion has been caused. Additionally, in the present embodiment, when abnormal motion is detected, the display of the real-time graph 103 shown in FIG. 3 is held up under the condition that the graph obtained at the time of abnormal motion shown in FIG. 5 is displayed, and therefore when the alert 104 for abnormal motion is given, a doctor can check the alert 104 and confirm, in that place, what type of the abnormality has been caused to the biological motion targeted for the detection.

Additionally, even if the blood flow waveform, the displacement of the wall motion, and the amount of change in the cross-sectional area, are targeted for detecting abnormal motion, this real-time graph 103 operates similarly. In other words, when abnormal motion for the targeted organ is detected, the waveform targeted for determining abnormal motion in the blood flow waveform, the displacement of the wall motion, or the amount of change in the cross-sectional area, is displayed as a graph in which the waveform falls out of the threshold range corresponding to said waveform.

Figure 6:
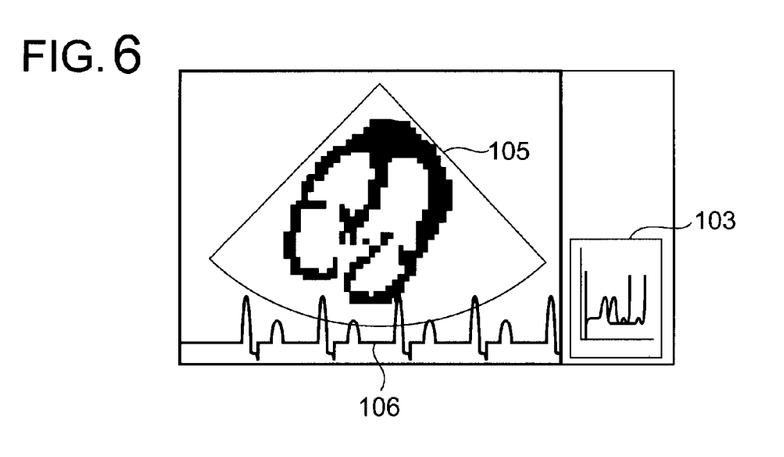
FIG. 6 is a display screen that automatically replays an abnormal condition.
Figure 7:
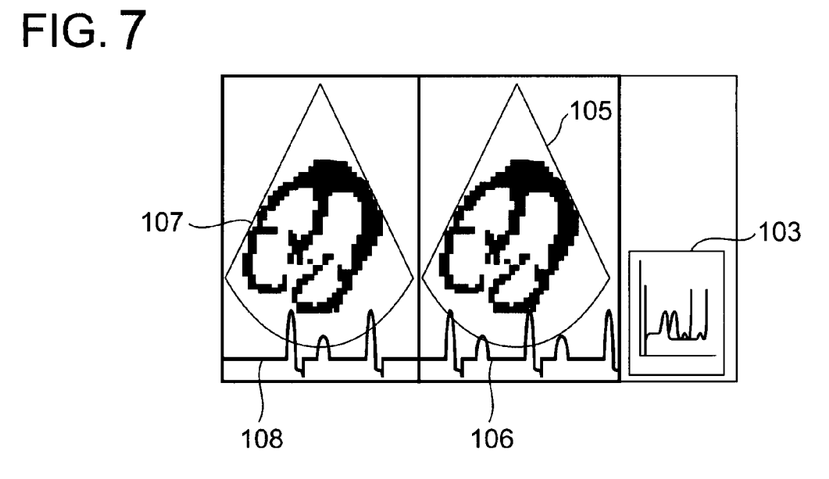
FIG. 7 is a display screen that displays, an automatically replayed abnormal condition and an automatically replayed normal condition by placing side-by-side thereof.

Additionally, the method for notifying a doctor of the condition of abnormal motion detection is not specially limited, and the display that is different from the present embodiment may be performed. For example, as shown in FIG. 6, the display controller 11 may instruct the display part 12 to repeatedly display the ultrasonic tomographic image 105 obtained in the abnormal condition and the electrocardiographic waveform 106 obtained at the time of abnormal motion. Furthermore, as shown in FIG. 7, the display controller 11 may instruct the display part 12 to display the ultrasonic tomographic image 107 and the electrocardiographic waveform 108, which have been obtained at the time of the normal motion, next to the ultrasonic tomographic image 105 and the electrocardiographic waveform 106, which have been obtained at the time of abnormal motion. At this stage, when the display controller 11 instructs the display part 12 to display the ultrasonic tomographic image 107 and the electrocardiographic waveform 108, which have been obtained at the time of the normal motion, next to the ultrasonic tomographic image 105 and the electrocardiographic waveform 106, which have been obtained at the time of abnormal motion, arrangement with reference to the starting reference position of the electrocardiographic waveform (in the case of the present embodiment, R-wave is used) allows the display part 12 to synchronously display the ultrasonic tomographic image 107 and the electrocardiographic waveform 108, which have been obtained at the time of the normal motion, next to the ultrasonic tomographic image 105 and the electrocardiographic waveform 106, which have been obtained at the time of abnormal motion. As described above, the ultrasonic tomographic image 105 and the electrocardiographic waveform 106, which have been obtained at the time of abnormal motion is repeatedly displayed, so a doctor can more visually understand the change and abnormality for the biological motion. Furthermore, the ultrasonic tomographic image 107 and the electrocardiographic waveform 108, which have been obtained at the time of the normal motion, are placed side-by-side, so a doctor can recognize the abnormal condition easily. This display method can be applied similarly, even if the blood flow waveform, the displacement of the wall motion, or the amount of change in the cross-sectional area, is targeted for detecting abnormal motion.

Additionally, in the present embodiment, the ultrasonic tomographic image obtained at the time of abnormal motion detection is displayed by using the images stored in the second memory 10. Meanwhile, this may be configured so that the execution controller 6 generates the image data using raw data stored in the first memory 4 at the time of detecting abnormal motion, transmits that image to the display controller 11, and instructs the display part 12 to display that. The same operation will be performed even if the blood flow waveform, the displacement of the wall motion, or the amount of change in the cross-sectional area, is targeted for detecting abnormal motion.

Figure 8:
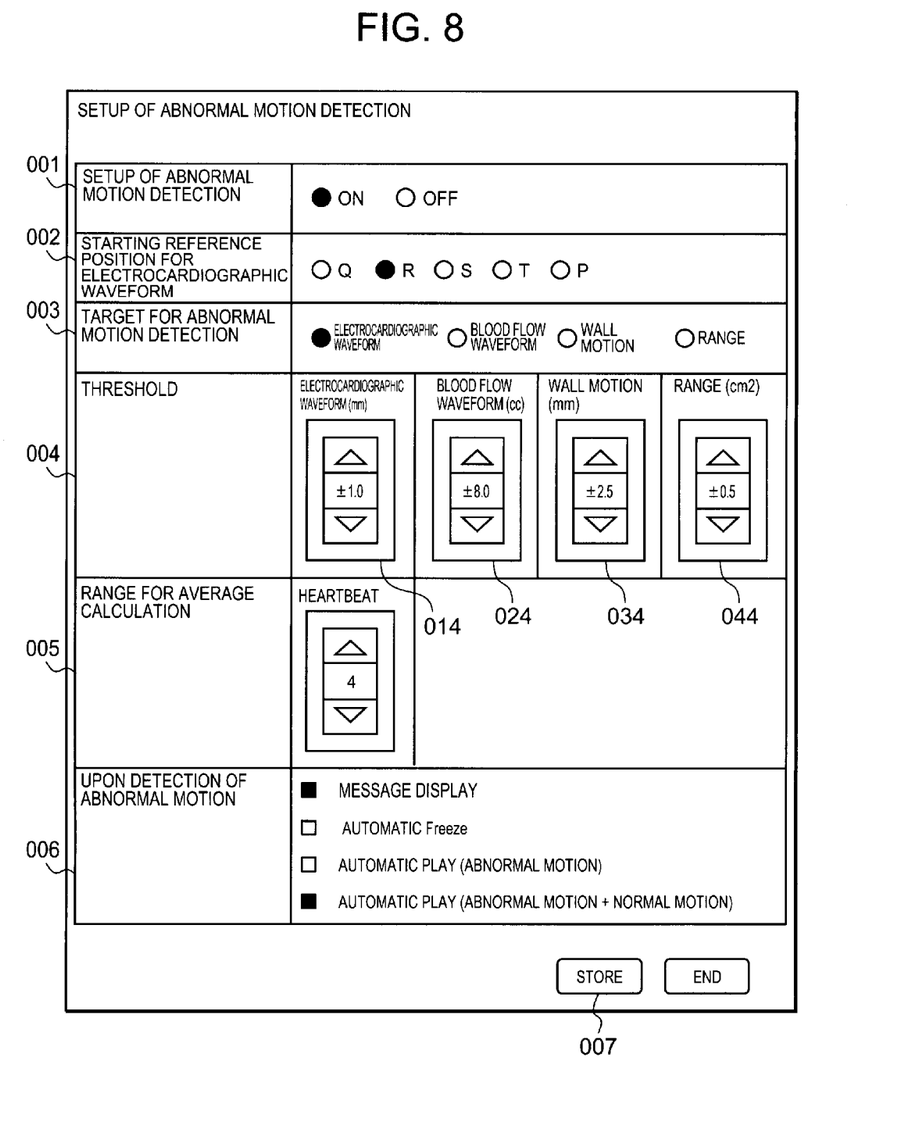
FIG. 8 is an example of a screen for setting up abnormal motion detection.

Additionally, for detection setup of abnormal motion by the operation part 5, a setup screen as shown in FIG. 8 may be used. Then, this setup screen format may be preliminarily included in the display controller 11 to instruct the display part 12 to display this setup screen. 001 is a button for setting whether abnormal motion detection is enabled. 002 is a button for setting where the starting reference position for the abovementioned electrocardiographic waveform is positioned. 003 is a button for determining the type of biological motion targeted for abnormal motion detection. In this figure, a range represents the amount of change. 004 is a button for determining the threshold used for determining abnormal motion for various biological motions. 005 is a button for setting the range for calculating the abovementioned average, and 006 is a button for setting a response given at the time of detecting abnormal motion. For 006, a message display is intended to display an alert 104 on the display part 12 for abnormal motion (refer to FIG. 3). An automatic freeze is intended to continuously hold up and display the screen in the condition in which abnormal motion is detected at the time of abnormal motion detection. An automatic play (abnormal motion) is intended to repeatedly display the motion for the ultrasonic tomographic image 105 and the electrocardiographic waveform 106, detected at the time of detecting abnormal motion (refer to FIG. 6). An automatic play (abnormal motion+normal motion) is intended to repeatedly display the motion of the ultrasonic tomographic image 105 and the electrocardiographic waveform 106, which have been obtained during abnormal motion, next to the motion of the ultrasonic tomographic image 107 and the electrocardiographic waveform 108, which have been obtained during normal motion (refer to FIG. 7). Then, detection setup of abnormal motion is set ON in 001 of the setup screen shown in FIG. 8, which is displayed on the operation part 5, and then scanning is started by placing the ultrasonic probe 1 on the subject, so abnormal motion detection is initiated. As used herein, the setting of ON in 001 means that abnormal motion detection is enabled, and OFF means that abnormal motion detection is disabled. If OFF is selected in 001, the selections from 002 to 006 will be hidden or grayed out so that setup cannot be performed. Subsequently, abnormal motion detection setup is stored in the memory 63 located in the execution controller 6 by pressing a storage button shown with 007 in FIG. 8.

Figure 9:
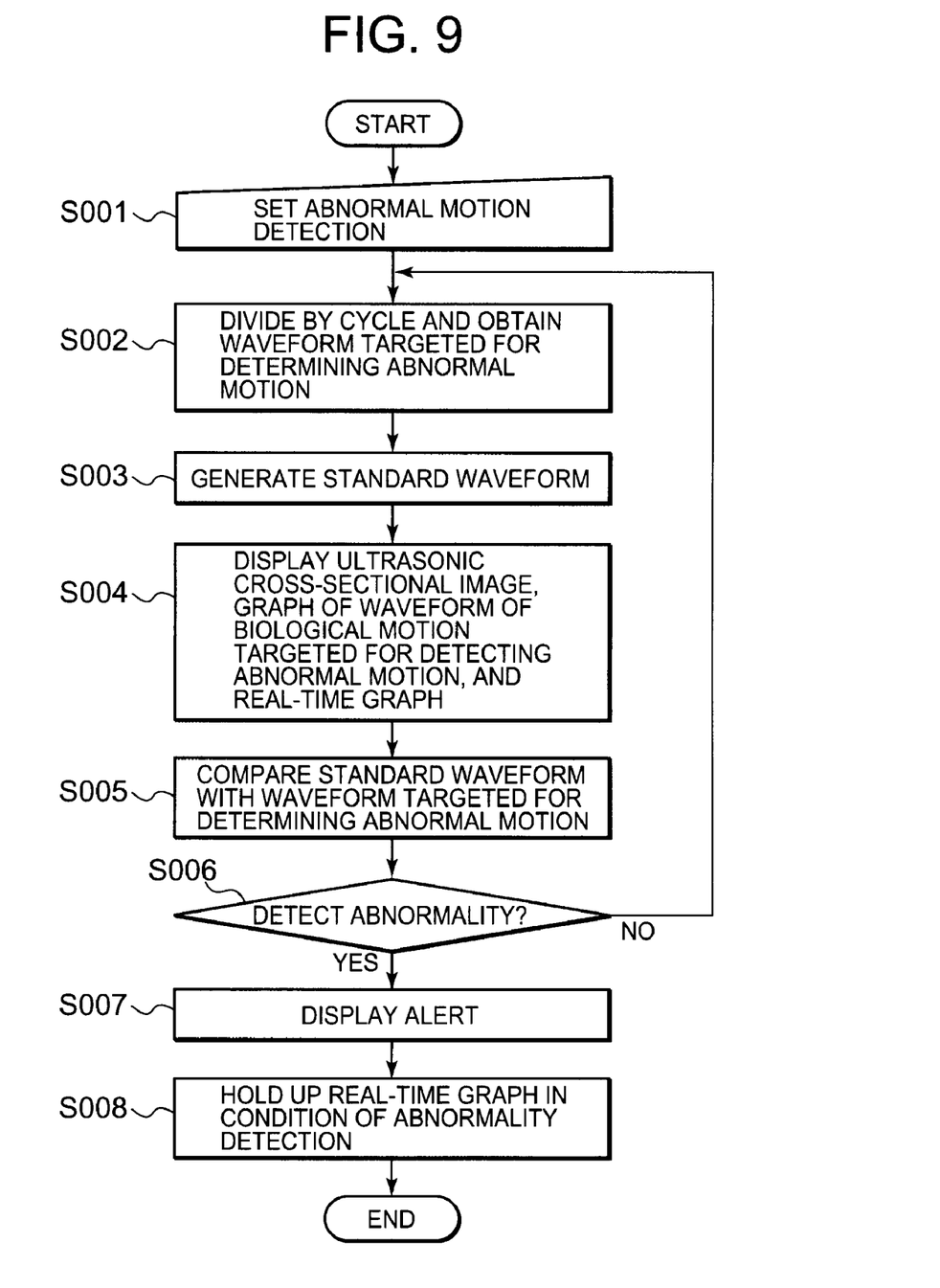
FIG. 9 is a flow chart illustrating an operation of abnormal motion detection.

Turning to FIG. 9, the operational flow for abnormal motion detection. FIG. 9 is a flow chart illustrating the operation of abnormal motion detection.

Step S001: A doctor inputs a setup for abnormal motion detection using the operation part 5.

Step S002: Based on the object targeted for abnormal motion detection and the reference position of the electrocardiographic waveform, which have been inputted from the operation part 5, the cycle generator 64 generates the electrocardiographic waveform, the blood flow waveform, the displacement of the wall motion, or the amount of change in the cross-sectional area, which is divided by individual cycles, by using the information about the biological motion received from the biological motion-measuring part 5, and then obtains the electrocardiographic waveform, the blood flow waveform, the displacement of the wall motion, or the amount of change in the cross-sectional area, which is targeted for determining abnormal motion.

Step S003: The standard waveform generator 62 generates the standard waveform, based on the range for calculating the average that has been input from the operation part 5.

Step S004: The execution controller 6 displays the ultrasonic tomographic image stored in the second memory 10, and further displays the electrocardiographic waveform, the blood flow waveform, the displacement of the wall motion, or the amount of change in the cross-sectional area. Additionally, once the threshold that has been input from the operation part 5 is received, the execution controller 6 transmits, to the display controller 11, the standard waveform, the waveform targeted for determining abnormal motion, and the threshold range. The display controller 11 instructs the display unit 12 to display the real-time graph 103 using the standard waveform, the waveform targeted for determining abnormal motion, and the threshold range.

Step S005: The determining part 61 receives the threshold and compares the standard waveform with the waveform targeted for determining abnormal motion.

Step S006: As a result of the comparison by the determining part 61, if the difference between the standard waveform and the waveform targeted for determining abnormal motion does not exceed the threshold and thus abnormal motion for the targeted organ is not detected, the steps S002 to S005 will be repeated, and if it exceeds the threshold and thus abnormal motion for the targeted organ is detected, step S007 will be performed in succession.

Step S008: The display controller 11 receives, from the execution controller 6, the standard waveform obtained at the time of abnormal motion detection, the latest electrocardiographic waveform obtained at the time of abnormal motion detection 202, and the threshold range 203, instructs the display part 12 to display the real-time graph 103, and then holds up the real-time graph 103 in that condition. In this step, if the blood flow waveform, the displacement of the wall motion, or the amount of change in the cross-sectional area, is targeted for detecting abnormal motion, the real-time graph 103 corresponding thereto is displayed.

As described above, the ultrasonic diagnostic apparatus according to the present embodiment, not only displays the ultrasonic tomographic image generated by ultrasonically scanning the subject, but also superposes and displays the measured waveform and the standard waveform. This makes it possible to instantly realize the change of the measured waveform for the target organ of the subject, so contribute to a prompt diagnosis. Additionally, the difference between the measured waveform and the standard waveform can be realized at a glance, and therefore the change of the measured waveform can be objectively realized, which contributes to an accurate diagnosis. Furthermore, as commonly observed in the circulatory organ field, an ischemic heart disease such as an allorhythmic pulse and a cardiac infarct, and a cardiomyopathy such as a valvular disorder and a dilated type, cause the deviation in the electrocardiographic waveform seen as the symptom thereof, therefore substantially contributing to the diagnosis for those diseases. Further, the ultrasonic tomographic image and the electrocardiographic waveform at the time of abnormality can be repeatedly displayed, so it is possible to certainly understand the condition for the targeted site that causes the abnormality. Since the selection for the measured waveform targeted for detecting the abnormality and the condition setup necessary for detecting the abnormality such as a threshold setup, can be also easily performed, abnormal motion detection for the measured waveform can be easily performed in response to operator's request.

Furthermore, in the abovementioned description, the standard waveform, the threshold range, and the current waveform are displayed by means of superposition, while the abnormality is automatically detected if the current waveform exceeds the threshold range has been described, but only superposing and displaying without detecting the abnormality are possible. In this case, a doctor ascertains the change in measured waveform by referring to a superposed and displayed graph, and determines whether it is abnormal after confirming whether the threshold is exceeded. Accordingly, the ultrasonic diagnostic apparatus that performs superposing and displaying without detecting the abnormality can contribute to an objective and prompt diagnosis.

What is claimed is:

1. An ultrasonic diagnostic apparatus that scans a cross-section of the target organ of a subject, generates an ultrasonic tomographic image based on an obtained echo signal, and displays the ultrasonic tomographic image on a display part, comprising:
   a biological motion-measuring part configured to measure cyclic biological motion of the targeted organ during the scanning so as to calculate a measured waveform that shows motion in relation to time used for the biological motion;
   a display controller configured to cause a display part to display a standard waveform for the measured waveform, and a measured waveform for the latest cycle by means of superposition, so as to match a specified time phase for each waveform; and
   a determination part configured to compare the standard waveform of the measured waveform with the measured waveform to determine whether the difference exceeds a threshold, wherein
   if the threshold is exceeded, thereby indicating an abnormality, the display controller is configured to maintain the display of the measured waveform at the time of exceeding the threshold and the display of the ultrasonic tomographic image at the time of exceeding the threshold.

2. The ultrasonic diagnostic apparatus according to claim 1,
   wherein the display controller is configured to cause the display part to further display a range below the threshold, based on the standard waveform.

3. The ultrasonic diagnostic apparatus according to claim 1,
   wherein the biological motion-measuring part is configured to measure an electrocardiographic waveform when a target organ of the subject is a heart.

4. The ultrasonic diagnostic apparatus according to claim 1,
   wherein the biological motion-measuring part is configured to calculate a blood flow waveform, a displacement of a heart wall motion, or an amount of change of a partial cross-sectional area of a heart, based on the echo signal, when a target organ of the subject is a heart.

5. The ultrasonic diagnostic apparatus according to claim 1,
   wherein the standard waveform is an average value for the measured waveforms from the specified cycle preceding the latest cycle to the previous cycle.

6. The ultrasonic diagnostic apparatus according to claim 1, further comprising:
   an alert part configured to alert when the threshold has been exceeded.

7. The ultrasonic diagnostic apparatus according to claim 1, further comprising:
   a first memory configured to store the cyclic measured waveform that has been measured; and
   a second memory configured to store the ultrasonic tomographic image that has been generated, wherein in case the threshold has been exceeded, the display controller performs:
   obtaining the measured waveform of exceeding the threshold from the first memory;
   obtaining the ultrasonic tomographic image of exceeding the threshold from the second memory;
   synchronizing the ultrasonic tomographic image with other the ultrasonic tomographic images; and
   superposing them to be displayed on the display part.

8. The ultrasonic diagnostic apparatus according to claim 1,
   wherein the display controller is configured to display the ultrasonic tomographic image of exceeding the threshold by generating the image from the obtained echo signal.

9. The ultrasonic diagnostic apparatus according to claim 1, further comprising:
   an operation part configured to set thresholds respectively for passed times of cyclic biological motion of the subject tissue, wherein
   the determination part is configured to compare the standard waveform of the measured waveform with the measured waveform to determine whether the difference exceeds a threshold or not.

10. A method for displaying a diagnostic image that scans a cross-section of a target organ of a subject, generates an ultrasonic tomographic image based on an obtained echo signal, and displays the ultrasonic tomographic image on a display part, comprising:
    measuring cyclic biological motion of the targeted organ during the scanning, so as to calculate a measured waveform that shows motion in relation to time used for the biological motion;
    displaying a standard waveform for the measured waveform, and a measured waveform for the latest cycle by means of superposition, so as to match a specified time phase for each waveform; and
    comparing the standard waveform of the measured waveform with the measured waveform to determine whether the difference exceeds a threshold or not, wherein
    if the threshold is exceeded, thereby indicating an abnormality, the display of the measured waveform at the time of exceeding the threshold and the display of the ultrasonic tomographic image at the time of exceeding the threshold are maintained.

11. The method for displaying a diagnostic image according to claim 10, comprising:
    displaying a range below the threshold, based on the standard waveform.

12. The method for displaying a diagnostic image according to claim 10,
wherein an electrocardiographic waveform is measured for the biological motion-measurement, when a target organ of the subject is a heart.

13. The method for displaying a diagnostic image according to claim 10,
wherein a blood flow waveform, a displacement of a heart wall motion, or an amount of change of a partial cross-sectional area of a heart is calculated for the biological motion-measurement, based on the echo signal, when a target organ of the subject is a heart.

14. The method for displaying a diagnostic image according to claim 10,
wherein the standard waveform is an average value for the measured waveforms from the specified cycle preceding the latest cycle to the previous cycle.

15. The method for displaying a diagnostic image according to claim 10, further comprising:
alerting the operator when the threshold has been exceeded.

16. The method for displaying a diagnostic image according to claim 10, further comprising:
storing, in a first memory, the cyclic measured waveform that has been measured; and
storing, in a second memory, the ultrasonic tomographic image that has been generated, wherein in case the abnormal motion has been determined, the method further comprising:
obtaining the measured waveform of exceeding the threshold from the first memory;
obtaining the ultrasonic tomographic image of exceeding the threshold from the second memory;
synchronizing the ultrasonic tomographic image with the other ultrasonic tomographic images; and
superposing them to be displayed on the display part.

17. The method for displaying a diagnostic image according to claim 10, further comprising:
displaying the ultrasonic tomographic image of exceeding the threshold, by generating the image from the obtained echo signal.

18. A method for displaying a diagnostic image according to claim 10, further comprising:
setting thresholds respectively for passed times of cyclic biological motion of the subject tissue, wherein
comparing the standard waveform of the measured waveform with the measured waveform to determine whether the difference exceeds a threshold or not.

19. A medical apparatus, comprising:
a biological motion-measuring part configured to measure cyclic biological motion of the targeted organ during scanning so as to calculate a measured waveform that shows the motion in relation to time used for the biological motion;
a display controller configured to cause a display part to display a standard waveform of the measured waveform, and a measured waveform for the latest cycle by means of superposition, so as to match a specified time phase for each waveform; and
a determination part configured to compare the standard waveform of the measured waveform with the measured waveform to determine whether the difference exceeds a threshold or not, wherein
if the threshold is exceeded, thereby indicating an abnormality, the display controller is configured to maintain the display of the measured waveform at the time of exceeding the threshold and the display of the ultrasonic tomographic image at the time of exceeding the threshold.

20. The medical apparatus according to claim 19, further comprising:
an operation part configured to set thresholds respectively for passed times of cyclic biological motion of the subject tissue, wherein
the determination part is configured to compare the standard waveform of the measured waveform with the measured waveform to determine whether the difference exceeds a threshold or not.

* * * * *